(12) United States Patent
Kumazawa

(10) Patent No.: US 12,298,250 B2
(45) Date of Patent: May 13, 2025

(54) FLOW ANALYSIS DEVICE AND FLOW ANALYSIS METHOD

(71) Applicant: BL TEC K.K., Osaka (JP)

(72) Inventor: Yorihiro Kumazawa, Tokyo (JP)

(73) Assignee: BL TEC K.K., Osaka (JP)

( * ) Notice: Subject to any disclaimer, the term of this patent is extended or adjusted under 35 U.S.C. 154(b) by 0 days.

(21) Appl. No.: 18/859,282

(22) PCT Filed: Apr. 28, 2022

(86) PCT No.: PCT/JP2022/019298
§ 371 (c)(1),
(2) Date: Oct. 23, 2024

(87) PCT Pub. No.: WO2023/209956
PCT Pub. Date: Nov. 2, 2023

(65) Prior Publication Data
US 2025/0110056 A1    Apr. 3, 2025

(51) Int. Cl.
*G01N 33/20* (2019.01)
*G01N 21/71* (2006.01)
(Continued)

(52) U.S. Cl.
CPC ........... *G01N 21/718* (2013.01); *G01N 33/18* (2013.01); *G01N 33/20* (2013.01); *H01J 49/105* (2013.01)

(58) Field of Classification Search
CPC ...... G01N 33/18; G01N 33/20; G01N 33/203; G01N 21/718; H01J 49/105
(Continued)

(56) References Cited

U.S. PATENT DOCUMENTS 4,014,652 A * 3/1977 Ishibashi ................ G01N 35/08
422/82
5,420,039 A   5/1995 Renoe et al.
(Continued)

FOREIGN PATENT DOCUMENTS

CN    207816690    9/2018
GB    2321703 A * 8/1998
(Continued)

OTHER PUBLICATIONS

International Search Report for PCT/JP2022/019298 and its English translation, dated Jul. 5, 2022, 4 pages.
(Continued)

*Primary Examiner* — Maureen Wallenhorst
(74) *Attorney, Agent, or Firm* — Casimir Jones, S.C.; Robert A. Goetz

(57) ABSTRACT

An object is to provide a flow analyzer which makes it possible to, without carrying out a complicated pretreatment, analyze mercury and analyze a sample containing mercury with accuracy equivalent to that of a conventional method. The object is attained by a flow analyzer including a sample introduction section (1), a reagent introduction section (3), and an analysis section (4), the flow analyzer further including: a heating section (5) that carries out a heat treatment with respect to a sample to which a reagent has been added;

(Continued)

a cooling section (6) that cools the sample which has been subjected to the heat treatment and which is transferred inside a tube; and a gas-liquid separation section (7) that removes gas which is present in the tube after cooling.

11 Claims, 5 Drawing Sheets

(51) Int. Cl.
  *G01N 33/18* (2006.01)
  *H01J 49/10* (2006.01)
(58) Field of Classification Search
  USPC ............... 436/52, 53, 73, 81, 164, 173, 180; 422/81, 82, 82.05
  See application file for complete search history.

(56) References Cited

U.S. PATENT DOCUMENTS

| | | | | |
|---|---|---|---|---|
| 11,623,218 | B2* | 4/2023 | Nishimura | G01N 33/1813 422/78 |
| 11,906,407 | B2* | 2/2024 | Nishimura | G01N 33/1813 |
| 2004/0048291 | A1 | 3/2004 | Hobolth | |
| 2023/0035345 | A1 | 2/2023 | Nishimura | |
| 2023/0038524 | A1 | 2/2023 | Nishimura et al. | |

FOREIGN PATENT DOCUMENTS

| | | |
|---|---|---|
| JP | 06-292885 | 10/1994 |
| JP | 10-048221 | 2/1998 |
| JP | 2000-055850 | 2/2000 |
| JP | 2004-515773 | 5/2004 |
| JP | 6903366 | 7/2021 |
| JP | 6947463 | 10/2021 |
| WO | 2021/153442 A1 * | 8/2021 |
| WO | 2021/205953 A1 * | 10/2021 |

OTHER PUBLICATIONS

The Ministry of Health, Labour and Welfare Notification No. 261, 2003, Appended Table 7, 89 pages, Partial English translation.
The Environment Agency Notification No. 59, 1971, Appended Table 2, 6 pages, Partial English translation.
Written Opinion for PCT/JP2022/019298 and its English translation (International Preliminary Report on Patentability), dated Jul. 5, 2022, 9 pages.

* cited by examiner

FLOW ANALYSIS DEVICE AND FLOW ANALYSIS METHOD

TECHNICAL FIELD

The present invention relates to a flow analyzer and a flow analysis method, in particular, a flow analyzer and a flow analysis method in each of which an analysis target is mercury.

BACKGROUND ART

As mercury was confirmed to be highly toxic, emissions and releases of mercury have been regulated in recent years. The Minamata Convention, which entered into force in 2017, prescribes the prohibition of mining of mercury and the regulations of the import and export of mercury and the like, with the aim of protecting the human health and the environment from the anthropogenic emissions and releases of mercury and mercury compounds. The EU also strictly regulates the use, the introduction, etc. of mercury under the RoSH Directive.

Since mercury relatively easily vaporizes, a reduction vaporization atomic absorption method, a reduction vaporization atomic fluorescence method, a burning vaporization-gold amalgam-atomic absorption method, and the like are used to analyze mercury. For example, the Ministry of Health, Labour and Welfare Notification No. 261, 2003, which prescribes a water quality inspection method based on the Water Supply Act, prescribes, in Appended Table 7, that mercury be inspected by the reduction vaporization atomic absorption method (see Non-Patent Literature 1). Further, the Environmental Quality Standards regarding Water Pollution prescribed in the Environment Agency Notification No. 59, 1971 also prescribes, in Appended Table 2, that mercury be measured by the reduction vaporization atomic absorption method (see Non-Patent Literature 2).

As a method for continuously analyzing a metal element in a sample, there is known a flow analysis method in which a sample is continuously introduced into a tube, a reagent is introduced into the tube inside which the sample flows so that the sample and the reagent are reacted with each other, and analysis data is continuously measured in an analysis section (for example, Patent Literatures 1 and 2).

CITATION LIST

Patent Literature

[Patent Literature 1]
  Japanese Patent No. 6947463
[Patent Literature 2]
  Japanese Patent No. 6903366

Non-Patent Literature

[Non-patent Literature 1]
  The Ministry of Health, Labour and Welfare Notification No. 261, 2003, Appended Table 7
[Non-patent Literature 2]
  The Environment Agency Notification No. 59, 1971, Appended Table 2

SUMMARY OF INVENTION

Technical Problem

However, a conventional mercury analysis method as described above needs an extremely complicated procedure for pretreating a sample.

An aspect of the present invention has been developed in view of the above problem, and the object thereof is to provide a flow analyzer and a flow analysis method each of which makes it possible to, without carrying out a complicated pretreatment of a sample, analyze the mercury and analyze the sample, which contains mercury, with accuracy equivalent to that of the conventional method.

Solution to Problem

In order to solve the problem, the inventor of the present invention considered that continuously carrying out operations from a pretreatment of a sample to an analysis of the sample in a closed system by a flow analysis method would make it possible to analyze mercury without carrying out a complicated pretreatment.

However, when the inventor of the present invention actually carried out a flow analysis method in such a manner that a sample containing mercury was continuously introduced into a tube, a reagent was introduced into the tube inside which the introduced sample flowed, the sample and the reagent were heated so that the sample and the reagent were reacted with each other, and analysis data was continuously measured in an analysis section, it was not possible to appropriately analyze the mercury.

Thus, the inventor of the present invention conducted diligent studies. As a result, when the inventor of the present invention carried out a flow analysis method in such a manner that a heat treatment was carried out with respect to a sample to which a reagent had been added and then the sample which had been subjected to the heat treatment and which was transferred inside a tube was cooled in a cooling section provided, the inventor of the present invention surprisingly found it possible to continuously analyze mercury in the sample with accuracy equivalent to that of the conventional method without carrying out a complicated pretreatment.

That is, a flow analyzer in accordance with an embodiment of the present invention is a flow analyzer including: a sample introduction section that is for introducing a sample into a tube; a reagent introduction section that adds a reagent to the sample which is transferred inside the tube; and an analysis section that quantitatively or qualitatively analyzes the sample to which the reagent has been added, the flow analyzer further including: a heating section that carries out a heat treatment with respect to the sample to which the reagent has been added; a cooling section that cools the sample which has been subjected to the heat treatment and which is transferred inside the tube; and a gas-liquid separation section that removes gas which is present in the tube after cooling.

A flow analysis method in accordance with an embodiment of the present invention is a flow analysis method including: a sample introduction step of introducing a sample into a tube; a reagent addition step of adding a reagent to the sample which is transferred inside the tube; and an analysis step of quantitatively or qualitatively analyzing the sample to which the reagent has been added, the flow analysis method further including: a heating step of carrying out a heat treatment with respect to the sample to which the reagent has been added; a cooling step of cooling the sample which has been subjected to the heat treatment and which is transferred inside the tube; and a gas-liquid separation step of removing gas which is present in the tube after cooling.

Advantageous Effects of Invention

An embodiment of the present invention brings about an effect that it is possible to provide a flow analyzer and a flow analysis method each of which makes it possible to, without carrying out a complicated pretreatment, analyze mercury and analyze a sample containing mercury with accuracy equivalent to that of the conventional method.

DESCRIPTION OF EMBODIMENTS

The following description will discuss embodiments of the present invention in detail. Note, however, that the present invention is not limited to the embodiments, and can be altered within the scope of the matters described herein. The present invention also encompasses, in its technical scope, any embodiment derived by combining, as appropriate, technical means disclosed in differing embodiments. Note that all academic and patent literatures cited herein are incorporated herein by reference. Note also that any numerical range expressed as "A to B" means "not less than A and not more than B (i.e., a range from A to B which includes both A and B)" unless otherwise specified in the present specification.

<1> Flow Analyzer

A flow analyzer in accordance with an embodiment of the present invention includes: a sample introduction section that is for introducing a sample into a tube; a reagent introduction section that adds a reagent to the sample which is transferred inside the tube; and an analysis section that quantitatively or qualitatively analyzes the sample to which the reagent has been added, the flow analyzer further including: a heating section that carries out a heat treatment with respect to the sample to which the reagent has been added; a cooling section that cools the sample which has been subjected to the heat treatment and which is transferred inside the tube; and a gas-liquid separation section that removes gas which is present in the tube after cooling.

The flow analyzer brings about an effect that it is possible to, without carrying out a complicated pretreatment, analyze mercury and analyze a sample containing mercury with accuracy equivalent to that of the conventional method. Moreover, the flow analyzer makes it possible to prevent volatilization of mercury, because a sample is transferred inside the tube without being brought into contact with external air. Therefore, the flow analyzer makes it possible to carry out accurate measurement.

<1.1> Embodiment 1

Figure 1:
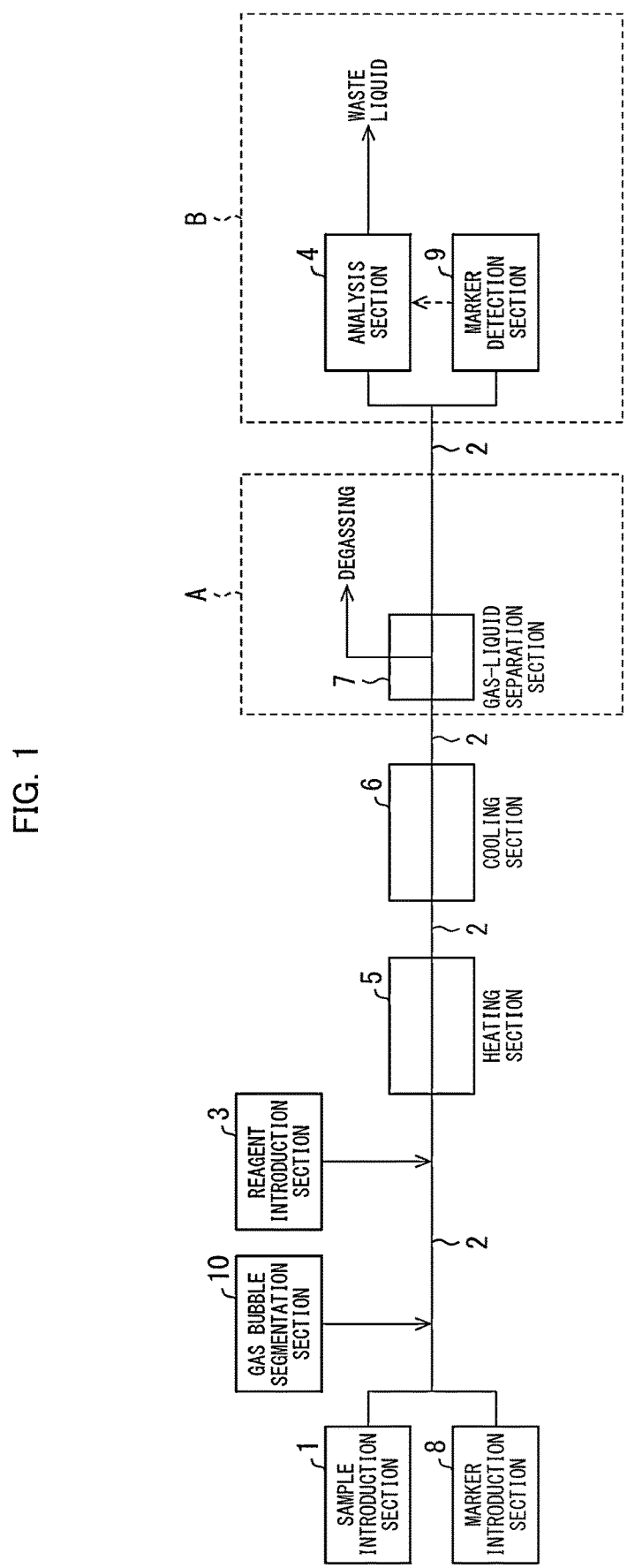
FIG. 1 is a drawing schematically illustrating a configuration of a flow analyzer in accordance with Embodiment 1 of the present invention.

An embodiment of the present invention will be described with reference to the drawings. FIG. 1 schematically illustrates a configuration of a flow analyzer in accordance with Embodiment 1 of the present invention.

The flow analyzer in accordance with Embodiment 1 of the present invention includes: a sample introduction section 1 that is for introducing a sample into a tube 2; a marker introduction section 8 that is for introducing a marker into the tube 2; a gas bubble segmentation section 10 that produces, inside the tube 2, a plurality of segments separated by gas bubbles, by carrying out gas bubble segmentation with respect to the sample and the marker which have been introduced into the tube 2; a reagent introduction section 3 that adds a reagent to a flow of the sample which is transferred inside the tube 2; a heating section 5 that carries out a heat treatment with respect to the sample which is transferred inside the tube 2 and to which the reagent has been added; a cooling section 4 that cools the sample which has been subjected to the heat treatment; a gas-liquid separation section 7 that removes gas which is present in the tube after cooling; an analysis section 4 that quantitatively or qualitatively analyzes the sample from which the gas has been removed by the gas-liquid separation section 7; and a marker detection section 9 that detects the marker and outputs a detection signal to the analysis section 4. The analysis section 4 acquires analysis data on the basis of the detection signal.

(Sample Introduction Section)

The sample introduction section 1 is a device for introducing a sample into the tube 2. For example, the sample introduction section 1 carries out sampling of a sample, and introduces the sample into the tube 2. In an embodiment of the present invention, the sample introduction section 1 includes a thief tube in which the sample is led to the tube 2 and a sampling pump which imparts a suction force to the thief tube. By the sampling pump, the sample is introduced into the tube 2 at a given flow rate.

(Marker Introduction Section)

The marker introduction section 8 is a device for introducing a marker into the tube 2. In an embodiment of the present invention, the marker introduction section 8 includes a thief tube in which the marker is led to the tube 2 and a pump which imparts a suction force to the thief tube. The marker only needs to contain a substance which can be detected by the marker detection section 9, and may be the substance or may be alternatively a solution containing the substance or may be alternatively a dispersion containing the substance.

Note, here, that the marker introduction section 8 and the sample introduction section 1 are configured such that the marker and a given number of samples which given number is one or more are capable of being alternately introduced into the tube 2. That is, the introduction of the marker into the tube 2 by the marker introduction section 8 and the introduction of the given number of samples, which given number is one or more, into the tube 2 by the sample introduction section 1 are alternately switched therebetween. This switching may be carried out manually or may be alternatively carried out automatically.

In a case where the marker introduction section 8 and the sample introduction section 1 are configured such that the marker and single samples are capable of being alternately introduced into the tube 2, the marker is introduced into the tube 2 prior to the introduction of each single sample. Then, for each single sample, the marker detection section 9 detects the marker and outputs, to the analysis section 4, a detection signal indicative of the detection of the marker, and the analysis section 4 acquires analysis data on the basis of the detection signal. This makes it possible to stably and continuously measure the sample, because, even in a case where it is not possible to send the sample stably and uniformly in time from a point of the introduction of the sample to the analysis section 4, a difference does not arise between a timing of appearance of a peak in the analysis data and a timing of the acquirement of the analysis data.

Alternatively, in a case where the marker introduction section 8 and the sample introduction section 1 are configured such that the marker and a given number of samples which given number is two or more are capable of being alternately introduced into the tube 2, the marker is introduced into the tube 2 once prior to the introduction of the given number of samples which given number is two or more. Then, the marker detection section 9 detects the marker and outputs, to the analysis section 4, a detection signal indicative of the detection of the marker, and the analysis section 4 sequentially acquires analysis data on the given number of samples on the basis of the detection signal. This makes it possible to stably and continuously measure the samples, because, even in a case where it is not possible to send the samples stably and uniformly in time from the point of the introduction of the samples to the analysis section, a difference between a timing of appearance of a peak in the analysis data between a timing of the acquisition of the analysis data can be reduced to a certain range. The upper limit of the given number may be selected as appropriate, in accordance with the types of the samples, a method of pretreating the samples, and/or the like, and can be, for example, 80, 70, 50, 20, 15, or 10.

The marker which can be detected by the marker detection section 9 is not particularly limited, but is preferably a substance which is not contained in the sample and/or a substance other than a substance to be analyzed. The marker is also preferably a substance which is not decomposed by heat and a reagent which is added between the point of the introduction of the marker into the tube 2 and the marker detection section 9. For example, the marker can be a substance which can be detected by a spectrophotometer. Such a substance is also not particularly limited, and examples thereof include rhodium, palladium, nickel, copper, chromium, manganese, iodine, cobalt, nitrate ion, phosphate ion, and silicate ion. Alternatively, the above substance can be a substance which can be detected by a voltammeter. Such a substance is also not particularly limited, and examples thereof include copper, cadmium, nickel, mercury, arsenic, and selenium. Alternatively, the above substance can be a substance which can be detected by an ion electrode meter. Such a substance is also not particularly limited, and examples thereof include calcium, potassium, fluorine, and ammonia. Alternatively, the above substance can be a substance which can be detected by an ion chromatography. Such a substance is also not particularly limited, and examples thereof include ions of inorganic acid and ions of organic acid, phenol, hydrazine, amino acid, and polysaccharides. Alternatively, the above substance can be a substance which can be detected by a turbidimeter. Such a substance is also not particularly limited, and examples thereof include silica which is a fine particulate substance that is not dissolved by acid other than hydrofluoric acid. Alternatively, the above substance can be a substance which can be detected by a fluorophotometer. Such a substance is also not particularly limited, and examples thereof include benzene, coumarin, and naphthalene. Among these substances, rhodium, palladium, cobalt, nickel, copper, and the like are particularly preferable as the marker, from the viewpoint of easiness of detection.

(Gas Bubble Segmentation Section)

Figure 5:
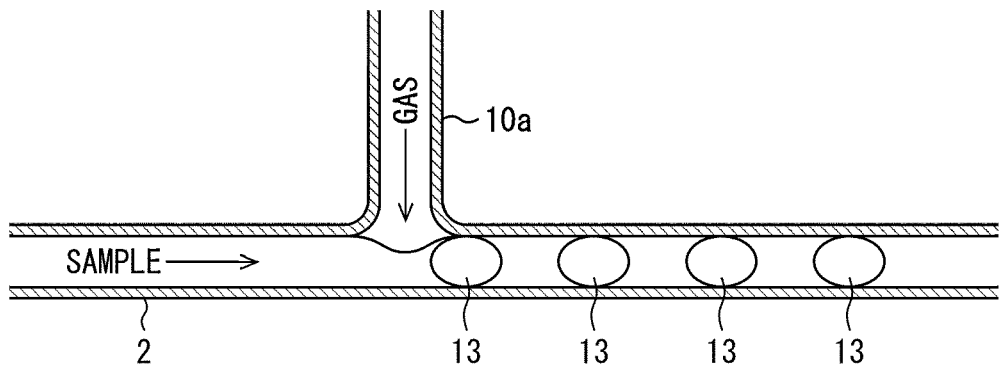
FIG. 5 is a drawing schematically illustrating how a plurality of segments which are separated by gas bubbles are produced inside a tube by a gas bubble segmentation section in a flow analyzer in accordance with an embodiment of the present invention.

The gas bubble segmentation section 10 is a device for producing, inside the tube 2, a plurality of segments separated by gas bubbles 13, by carrying out gas bubble segmentation with respect to the sample and the marker which have been introduced into the tube 2, as illustrated in FIG. 5. In an embodiment of the present invention, the gas bubble segmentation section 10 includes a gas introduction tube 10a in which gas is led to the tube 2 and a gas introduction pump (not illustrated) which imparts a suction force to the gas introduction tube. By carrying out the gas bubble segmentation, it is possible to suitably mix the reagent and the like, due to a turbulent flow in a segmented liquid which is divided by the gas bubbles 13. Since the segmented liquid, i.e., the sample which forms each of the segments that are separated by the gas bubbles 13, is divided by the gas bubbles 13 and independently flows inside the tube 2, it is possible to prevent interdiffusion of the sample. The gas for the gas bubble segmentation is preferably air, but may be an inert gas(es) such as argon and/or helium. Various gases such as nitrogen and oxygen can be also used. Each of these gases may be used solely or two or more of these gases may be mixed and used. A method of, in this manner, introducing a reagent into a continuous flow of a sample inside a tube which sample is segmented by gas bubbles, carrying out a reaction operation, removing the gas bubbles, and then carrying out an analysis in a detector which is provided downstream is referred to as a continuous flow analysis method (CFA). Note that, in the present specification, the term "downstream" means being downstream of a flow of a sample inside a tube for a flow analysis.

(Reagent Introduction Section)

The reagent introduction section 3 is a device for adding the reagent to the flow of the sample that is transferred inside the tube 2. The reagent introduction section 3 includes a reagent introduction tube in which the reagent is led to the tube 2 and a reagent introduction pump which imparts a suction force to the reagent introduction tube. The reagent can be a reagent which is added during the pretreatment of the sample. The reagent is not particularly limited, and examples thereof include: acid such as nitric acid, hydrochloric acid, sulfuric acid, perchloric acid, phosphoric acid, hydrogen peroxide, and hydrofluoric acid; stabilizers for mercury, such as L-cysteine and gold; and alkali such as sodium hydroxide, potassium hydroxide, sodium peroxide, calcium carbonate, and sodium carbonate. Each of these reagents may be used solely or two or more of these reagents may be used in combination. In a case where two or more types of reagents are used, a plurality of reagent introduction sections 3 may be provided. Alternatively, in a case where at least two types of reagents, out of the two or more types of reagents, can be mixed and then introduced, the reagents which can be mixed may be mixed and then introduced from a single reagent introduction section 3. The reagent may be selected, as appropriate, in accordance with an analysis target, an analysis method, and the like, but more preferably contain nitric acid or a combination of nitric acid and hydrochloric acid, from the viewpoint of accurately analyzing mercury. In a case where the inductively coupled plasma mass spectrometry (ICP-MS) is used as an analysis method, the reagent preferably contains nitric acid or a combination of nitric acid and hydrochloric acid.

(Heating Section)

The heating section 5 is a device for carrying out a heat treatment with respect to the sample that is transferred inside the tube 2. The heating section 5 can be a thermostatic bath which includes a heater. Note, however, that a configuration of the heating section 5 is not limited to such a configuration, and the heating section 5 may be an ultrasonic decomposition device, a microwave, an autoclave decomposition device, or the like. In the heating section 5, the tube 2 may form, for example, a coil. In an embodiment of the present invention, the heating section 5 is provided downstream of the reagent introduction section 3. By heating the sample to which the reagent has been added, it is possible to promote a reaction between the sample and the reagent and thereby pretreat the sample. In the heating section 5, it is possible to carry out, for example, thermolysis or high-temperature and high-pressure decomposition of the sample.

A heating temperature in the heating section 5 only needs to be set such that, for example, the sample has a temperature of not lower than 50° C., not lower than 60° C., not lower than 70° C., or not lower than 80° C. The upper limit of the heating temperature is preferably not higher than 140° C., not higher than 130° C., or not higher than 120° C. A heating time during which the sample is heated is, for example, not shorter than 5 minutes, not shorter than 10 minutes, or not shorter than 20 minutes per unit of the sample introduced (a single sample). The upper limit of the heating time is, for example, not longer than 80 minutes, and more preferably not longer than 40 minutes. By setting the heating temperature and the heating time in the heating section 5 to fall within the above respective ranges, it is possible to sufficiently decompose a compound, including a mercury compound, in the sample.

Figure 6:
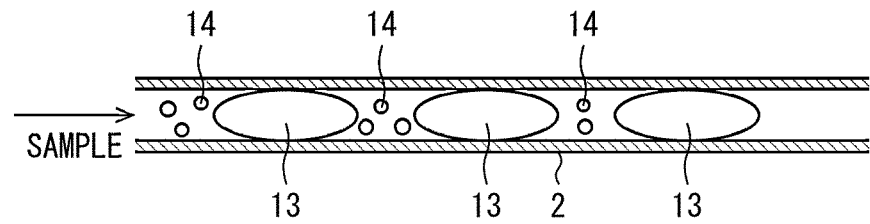
FIG. 6 is a drawing schematically illustrating gas bubbles inside a tube after a heat treatment in a flow analyzer in accordance with an embodiment of the present invention.

FIG. 6 is a drawing schematically illustrating the gas bubbles inside the tube after the heat treatment in the flow analyzer in accordance with an embodiment of the present invention. As illustrated in FIG. 6, the gas bubbles 13 which have been introduced by the gas bubble segmentation section 10 expand by the heat treatment. The reaction between the sample and the reagent may cause generation of gas, and, in this case, the gas thus generated also expand by the heat treatment. The gas which has been generated by the reaction and which has expanded disperse as gas bubbles 14 in the segmented liquid or unite with the gas bubbles 13 which have been introduced by the gas bubble segmentation section 10. At least a part of mercury contained in the sample at this time vaporizes by the heat treatment, and moves into the gas phase of the gas bubbles 13 or the gas bubbles 14.

In an example illustrated in FIG. 1, the flow analyzer includes a pretreatment unit which is constituted by a single reagent introduction section 3 and a single heating section 5 that is provided downstream of the single reagent introduction section 3. Alternatively, instead of the single reagent introduction section 3, a plurality of reagent introduction sections 3 may be provided upstream of the heating section 5 so that a plurality of reagents are added.

In the example illustrated in FIG. 1, the flow analyzer includes the pretreatment unit which is constituted by the single reagent introduction section 3 and the single heating section 5 that is provided downstream of the single reagent introduction section 3. Alternatively, provided may be one or more reagent introduction sections 3, a single heating section 5 that is located downstream of the one or more reagent introduction sections 3, and a reagent introduction section 3 that is located downstream of the single heating section 5 and upstream of the analysis section 4. The reagent introduction section 3 that is located downstream of the single heating section 5 and upstream of the analysis section 4 may add, for example, nitric acid, hydrochloric acid, or nitric acid and hydrochloric acid as the reagent. In a case where the inductively coupled plasma mass spectrometry (ICP-MS) is used, it is possible to more stably measure mercury by adding hydrochloric acid to a nitric acid solution at a point that is located upstream of the heating section 5 or at a point that is located downstream of the heating section 5 and upstream of the analysis section 4.

Further, in the example illustrated in FIG. 1, the flow analyzer includes a single pretreatment unit. Alternatively, the flow analyzer may include a plurality of pretreatment units, and, in this case, each of the plurality of pretreatment units may include a different number of reagent introduction sections 3. In a case where the flow analyzer includes a plurality of pretreatment units, it is possible to carry out a pretreatment which involves, for example, carrying out acidolysis under heating, adding acid again, and then carrying out acidolysis under heating. In a case where the flow analyzer includes a plurality of reagent introduction sections 3, reagents which are added by the plurality of reagent introduction sections 3 may be identical to or different from each other.

In the example illustrated in FIG. 1, the reagent introduction section 3 is provided downstream of the gas bubble segmentation section 10. Note, however, that disposition of the reagent introduction section 3 is not limited such disposition. The reagent introduction section 3 may be provided upstream of the gas bubble segmentation section 10. In a case where the flow analyzer includes a plurality of reagent introduction sections 3, the plurality of reagent introduction sections 3 may be provided upstream and downstream of the gas bubble segmentation section 10. Alternatively, there is also a case where the reagent which is introduced by the reagent introduction section 3 is a reagent for allowing the detection of the marker (e.g. coloring liquid). In such a case, the reagent introduction section 3 may be provided downstream of the heating section 5. Alternatively, one or more reagent introduction sections 3 each of which is for introducing the reagent that is used in the pretreatment may be provided upstream of the heating section 5, and one or more reagent introduction sections 3 each of which is for introducing the reagent that is used to allow the detection of the marker may be provided downstream of the heating section 5.

(Cooling Section)

The cooling section 6 is a device that cools the sample which has been subjected to the heat treatment by the heating section 5 and which is transferred inside the tube 2. The cooling section 6 preferably includes a tube which has a length of 0.5 m to 3.0 m and inside which the sample is transferred. The tube 2 is connected to both ends of the tube of the cooling section 6. The sample which has been subjected to the heat treatment by the heating section 5 and which is transferred inside the tube 2 is, as it is, continuously transferred inside the tube of the cooling section 6. The sample which has passed through the tube of the cooling section 6 continues to be continuously transferred inside the tube 2. In other words, the tube of the cooling section 6 serves as the tube 2. The tube 2 and each of the both ends of the tube of the cooling section 6 are connected to each other such that the sample and the gas which are transferred inside the tube are sealed in the tube. The inner diameter of the tube 2 and the inner diameter of the tube of the cooling section 6 may be equal to or different from each other, provided that the sample can be continuously transferred.

The sample which has been subjected to the heat treatment by the heating section 5 and which is transferred inside the tube 2 is introduced into the tube of the cooling section 6, and cooled while being transferred inside the tube of the cooling section 6. The length of the tube of the cooling section 6 is more preferably 0.7 m to 2.5 m, and even more preferably 1.0 m to 2.0 m. The length of the tube of the cooling section 6 is preferably not shorter than 0.5 m, because the sample which has been subjected to the heat treatment is sufficiently cooled while being transferred inside the tube of the cooling section 6. In a conventional flow analyzer which includes a gas-liquid separation section that is located downstream of a heating section, the length of a tube from the heating section to the gas-liquid separation section is typically 0.5 cm to 20 cm. In an analysis in which an analysis target is not mercury, it is not necessary to make the tube from the heating section to the gas-liquid separation section long. This is because there is not a problem that an element to be measured is removed together with gas even in a case where the gas is removed in a state where a sample inside the tube has a high temperature. In a case where mercury is to be measured and in a state where the temperature inside the tube is high, the mercury is contained in a gas phase. Therefore, by decreasing the temperature inside the tube so that the mercury is brought back to a liquid phase, it is possible to prevent the mercury from being removed together with the gas. Further, in a case where the length of the tube of the cooling section 6 is not longer than 3 m, time taken to transfer the sample is not too long. Therefore, it is possible to shorten the time needed for an analysis, and possible to make the device compact.

A cooling method in the cooling section 6 is not particularly limited, but examples thereof include: a method in which the tube 2 inside which the sample that has been subjected to the heat treatment is transferred is cooled by air; and a method in which the tube 2 is cooled by a cooling medium such as water (for example, a method in which the tube 2 is cooled by water, and a method in which the tube 2 is cooled by ice water).

The material of the tube of the cooling section 6 is not particularly limited, provided that the material is inactive with respect to the sample which is transferred inside the tube. Examples of the material include fluorine-based resins such as perfluoroalkoxyalkane (PFA) and polytetrafluoroethylene (PTFE); olefin-based resins such as polypropylene and polyethylene; glass; and PEEK resin (polyether ether ketone resin). Note that the material of the tube 2 in the flow analyzer in accordance with an embodiment of the present invention is also not particularly limited, provided that the material is inactive with respect to the sample which is transferred inside the tube. For example, a material similar to that of the tube of the cooling section 6 as described above can be used.

The inner diameter of the tube of the cooling section 6 is, but is not limited to, preferably 0.5 mm to 3.0 mm, more preferably 1.2 mm to 2.5 mm, even more preferably 1.5 mm to 2.3 mm, particularly preferably 1.8 mm to 2.2 mm, and most preferably 1.9 mm to 2.1 mm. In a case where the inner diameter is not less than 0.5 mm, it is possible to transfer the sample inside the tube at a moderate rate. In a case where the inner diameter is not more than 3.0 mm, the sample which is transferred inside the tube is more frequently brought into contact with a wall of the tube, so that it is possible to more rapidly cool the sample. Therefore, such an inner diameter is preferable.

Figure 10:
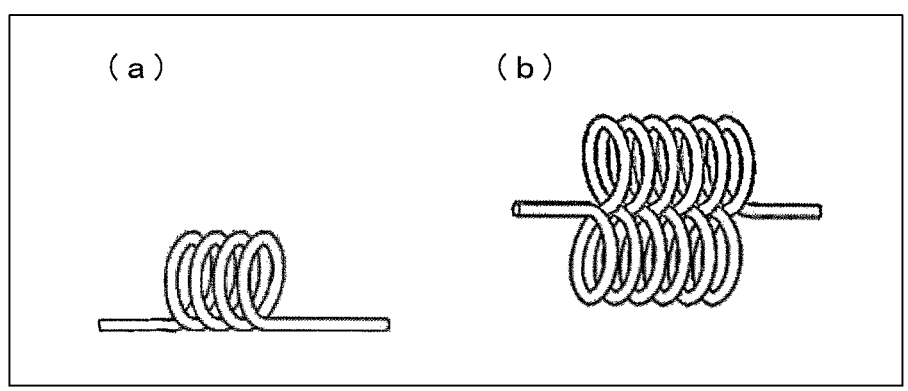
FIGS. 10 (a)-10 (b) are drawings illustrating an example of a coil part of a cooling section in a flow analyzer in accordance with an embodiment of the present invention.

The shape of the tube of the cooling section 6 is not particularly limited, and may be a linear shape or a curved shape. In particular, the tube preferably includes a coil part. The coil part has a shape of, for example, a helix, a figure-eight helix, or the like. FIG. 10 schematically illustrates examples of the coil part. (a) of FIG. 10 illustrates the coil part having a shape of a helix. (b) of FIG. 10 illustrates the coil part having a shape of a figure-eight helix. In a case where the tube of the cooling section 6 includes the coil part, the sample transferred inside the tube is transferred while being circulated inside the tube. This causes the sample to be stirred and mixed. Therefore, at the same time the sample is cooled, mercury in the gas phase is more likely to transition to the liquid phase. Thus, such a configuration is preferable, because it is possible to prevent a loss caused by vaporization of mercury and carry out an accurate analysis.

In a case where the tube of the cooling section 6 includes the coil part, the tube may be constituted solely by the coil part or may alternatively include the coil part and a linear part. From the viewpoint of carrying out a more accurate analysis, the tube more preferably includes the coil part and also the linear part. The reason therefor is not clear, but the following inference is derived. That is, since the sample is stirred and mixed in the coil part, the coil part has the function of cooling the sample and, at the same time, transitioning mercury in the gas phase to the liquid phase. Meanwhile, the linear part has the function of more efficiently cooling the sample. Therefore, by combining both the parts, it is possible to more effectively prevent a loss caused by vaporization of mercury. The disposition of the coil part and the linear part can be, but is not limited to, for example, such that the coil part is disposed downstream of the linear part. According to this configuration, it is considered that (i) the sample which has been subjected to the heat treatment is cooled mainly in the linear part and thereby mercury which has been present as gas in the sample becomes liquid and then (ii) in the coil part, the sample is stirred and mixed and the mercury transitions to the liquid phase. In such a case, the ratio between the length of the linear part of the tube and the length of the coil part of the tube is, for example, 1:1 to 10:1, and more preferably 2:1 to 5:2. Note, here, that the "length of the coil part" in the expression "ratio between the length of the linear part of the tube and the length of the coil part of the tube" is intended to be the length of the tube which forms the coil part, that is, the length of the tube in a case where the coil part is stretched linearly. In the configuration in which the coil part is disposed downstream of the linear part, a second linear part may be further present downstream of the configuration in which the coil part is disposed downstream of the linear part. In such a case, the ratio between the length of the linear part of the tube and the length of the coil part of the tube is intended to be the ratio between the length of the linear part which is located upstream of the coil part and the length of the coil part, and the length of the second linear part is not taken into consideration.

Alternatively, the configuration in which the coil part is disposed downstream of the linear part may be repeated a plurality of times, for example, 2 to 10 times. Also in such a case, the "length of the coil part" is as described above. A linear part which serves as the last stage may be further present downstream of a configuration in which the configuration in which the coil part is disposed downstream of the linear part is repeated a plurality of times. In such a case, the ratio between the length of the linear part of the tube and the length of the coil part of the tube is intended to be the ratio between the total length of the linear parts which are located upstream of the respective plurality of coil parts and the total length of the plurality of coil parts, and the length of the linear part at the last stage is not taken into consideration.

The number of turns of the helix, the figure-eight helix, and the like of the coil part is also not particularly limited. The number of turns is, for example, 1 turn to 20 turns, more preferably 2 turns to 10 turns, and even more preferably 4 turns to 7 turns. The number of turns is preferably not less than 1 turn, because the sample is stirred and mixed more uniformly and, therefore, at the same time the sample is cooled, mercury in the gas phase is more likely to transition to the liquid phase. The number of turns is preferably not more than 20 turns, because it is possible to make the device compact and shorten the time needed for an analysis.

In a case where the coil part has, for example, a shape of a helix, the outer diameter of the helix (referred to as "coil diameter") is, but is not particularly limited to, for example, 10 mm to 70 mm, more preferably 15 mm to 60 mm, even more preferably 20 mm to 50 mm, and most preferably 25 mm to 40 mm. The coil diameter is preferably not less than 10 mm, because it is possible to stably send the liquid. The coil diameter is preferably not more than 70 mm, because it is possible to mix the liquid more appropriately.

In a case where the coil part has, for example, a shape of a helix, the coil pitch of the helix is, but is not particularly limited to, for example, 0.7 mm to 40 mm, more preferably 0.8 mm to 30 mm, and even more preferably 0.9 mm to 25 mm. The coil pitch is preferably not less than 0.7 mm, because it is possible to form the coil part in which a tube having a preferable tube diameter is wound. Further, the coil pitch is preferably not more than 40 mm, because the coil part having such a coil pitch has a size with which the coil part does not take up much space.

In a case where the coil part has, for example, a shape of a figure-eight helix, the maximum length of the figure eight of the figure-eight helix is similar to the coil diameter in the case of the helix, and the pitch of the figure-eight helix is similar to the coil pitch in the case of the helix.

A cooling temperature in the cooling section 6 only needs to be set such that, for example, the sample has a temperature of not higher than 30° C., preferably not higher than 20° C., and more preferably not higher than 10° C. A cooling time during which the sample is cooled is not particularly limited, provided that the sample can be sufficiently cooled. The cooling time is, for example, not shorter than 2 minutes, not shorter than 3 minutes, or not shorter than 5 minutes per unit of the sample introduced. The upper limit of the cooling time is, for example, 15 minutes per unit of the sample introduced. By setting the cooling temperature and the cooling time in the cooling section 6 so as to fall within the above respective ranges, it is possible to form, into liquid, mercury which is present as gas in the sample.

The cooling section 6 is disposed between the heating section 5 and the gas-liquid separation section 7. The sample and the gas bubbles 13 and 14 which have been cooled by the cooling section 6 and which are transferred inside the tube 2 are transferred inside the tube 2 to the gas-liquid separation section 7.

(Gas-Liquid Separation Section)

Figure 7:
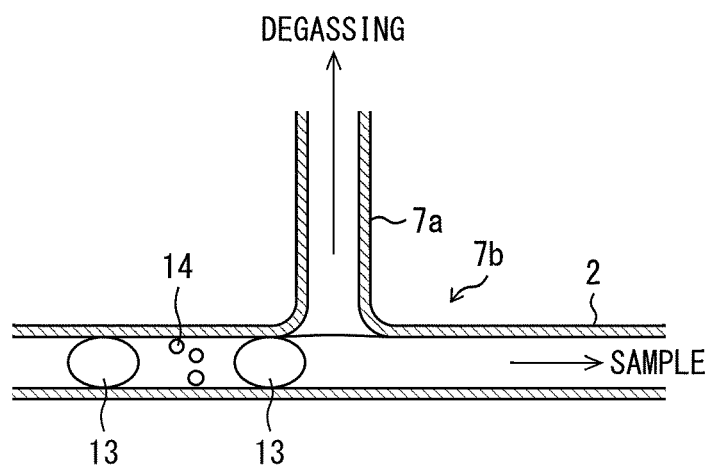
FIG. 7 is a drawing schematically illustrating how gas which is present in a tube is removed by a gas-liquid separation section in a flow analyzer in accordance with an embodiment of the present invention.

The gas-liquid separation section 7 is a device for sequentially removing the gas which is present inside the tube 2. FIG. 7 is a drawing schematically illustrating how the gas which is present inside the tube 2 is removed by the gas-liquid separation section 7. As illustrated in FIG. 7, the gas-liquid separation section 7 includes: a three-way tube 7b that includes (i) a tube (tube 2) inside which the sample continues to be transferred in a horizontal direction or a downward direction in a downstream direction of the tube 2 and (ii) a degassing tube 7a which branches upward; a pump (not illustrated) that imparts a suction force to the tube 2 inside which the sample continues to be transferred in the horizontal direction or the downward direction; and a degassing pump (not illustrated) that imparts a suction force to the degassing tube.

As illustrated in FIG. 7, the gas which is present in the tube 2 (gas bubbles 13 and 14) rises upward, and is therefore removed (degassing) through the degassing tube of the three-way tube which degassing tube branches upward.

(Analysis Section)

The analysis section 4 is a device which analyzes the sample to which the reagent has been added, which has been subjected to the heat treatment by the heating section 5, which has been cooled by the cooling section 6 after the heat treatment, and from which the gas has been removed by the gas-liquid separation section 7 after the cooling. In an embodiment of the present invention, the analysis section 4 can be an inductively coupled plasma mass spectrometer (ICP-MS). Note, however, that the analysis section 4 is not limited to such an analysis device, and may be any analysis device. The analysis section 4 may be, for example, an inductively coupled plasma optical emission spectrometer (ICP-OES), an atomic absorption photometer, an inductively coupled plasma triple quadrupole mass spectrometer, an ion electrode meter, or a spectrophotometer. The analysis section 4 is not limited to a device for detecting the presence or absence of mercury or measuring only the concentration of the mercury, and is also preferably a device which can collectively measure the other metal elements. The analysis is not limited to a quantitative analysis or a qualitative analysis.

(Marker Detection Section)

Between the gas-liquid separation section 7 and the analysis section 4, the marker detection section 9 is connected to a branch tube which is for extracting, from the tube 2, the sample and the marker which sequentially flow inside the tube 2. In other words, the tube 2 branches into two at a stage after the removal of the gas by the gas-liquid separation section 7 and prior to introduction of the sample into the analysis section 4, and one (referred to as "tube 2" even after the branching) is connected to the analysis section 4 while the other (referred to as "branch tube") is connected to the marker detection section 9. The marker detection section 9 continuously measures the liquid extracted from the tube 2 through the branch tube. When the marker detection section 9 detects the marker, the marker detection section 9 outputs the detection signal to the analysis section 4. Then, in an embodiment of the present invention, upon receipt of the detection signal, the analysis section 4 starts acquiring the analysis data. In an embodiment of the present invention, the marker detection section 9 is a spectrophotometer. In a case where the marker contains rhodium, the marker detection section 9 outputs, to the analysis section 4, the detection signal when the marker detection section 9 detects the rhodium. Note, however, that the marker detection section 9 is not limited to the spectrophotometer, and can be, for example, a voltammeter, an ion electrode meter, an ion chromatograph, a turbidimeter, or a fluorophotometer. The marker and the sample which sequentially flow are introduced into the analysis section 4 and the marker detection section 9 at the same timing through the tube 2 and the branch tube, respectively. Alternatively, the marker and the sample which sequentially flow may be introduced into the analysis section 4 and the marker detection section 9 at different timings, not at the same timing. In a case where the marker and the sample which sequentially flow are introduced into the analysis section 4 and the marker detection section 9 at different timings, the marker and the sample need to be introduced into the marker detection section 9 at a timing earlier than a timing at which they are introduced into the analysis section 4. In the above embodiment, the analysis section 4 is configured to start acquiring the analysis data upon receipt of the detection signal. However, the analysis section 4 may be set to start acquiring the analysis data a given time after the receipt of the detection signal.

In an embodiment of the present invention, the analysis section 4 and the marker detection section 9 are disposed in parallel as described above. Note, however, that the analysis section 4 and the marker detection section 9 may be disposed in series as in an embodiment illustrated in FIG. 4. In the embodiment illustrated in FIG. 4, the marker detection section 9 is disposed between the gas-liquid separation section 7 and the analysis section 4. At the stage after the removal of the gas by the gas-liquid separation section 7 and prior to the introduction of the sample into the analysis section 4, the marker detection section 9 continuously measures the liquid that is introduced thereinto through the tube 2, and outputs the detection signal to the analysis section 4 when the marker detection section 9 detects the marker. Then, after the receipt of the detection signal, the analysis section 4 starts acquiring the analysis data. In this case, it is only necessary to adjust a timing of a start of the acquisition of the analysis data so that the analysis section 4 can measure the sample which has reached the analysis section 4. For example, the analysis section 4 may be set to start acquiring the analysis data a given time after the receipt of the detection signal.

In an example illustrated in FIG. 1, the sample from which the gas has been removed by the gas-liquid separation section 7 is transferred to the marker detection section 9 or the analysis section 4 which are located downstream of the gas-liquid separation section 7. Between the gas-liquid separation section 7 and the marker detection section 9 or the analysis section 4, a mixing coil for further mixing the sample may be provided. The mixing coil is the tube 2 which is formed in a shape of a coil, and when the sample passes through the mixing coil, the sample which flows inside the tube 2 is mixed. The shape of the mixing coil is not particularly limited, but can be a shape that is similar to any of the shapes illustrated in FIG. 10.

In the flow analyzer in accordance with Embodiment 1 described above, the sample is continuously introduced into the tube, the gas bubble segmentation is carried out, the reagent is introduced, a reaction is promoted by the heating section, mercury which has vaporized is transitioned to the liquid phase by cooling the sample and the gas bubbles by the cooling section, and then the gas is removed by the gas-liquid separation section. This makes it possible to prevent a loss caused by vaporization of mercury and continuously measure the analysis data by the analysis section. Furthermore, the flow analyzer includes: the marker introduction section which is for introducing the marker into the tube; and the marker detection section which detects the marker and outputs the detection signal to the analysis section, and the analysis section acquires the analysis data on the basis of the detection signal. This makes it possible to stably and continuously measure the sample.

In general, in a case where a flow analyzer includes a gas-liquid separation section, a gas bubble segmentation device which newly leads gas to a tube is often provided downstream of the gas-liquid separation section. In the flow analyzer in accordance with an embodiment of the present invention, a gas bubble segmentation device which newly leads gas to the tube is not provided between the gas-liquid separation section and the analysis section. With this configuration, mercury in the sample is introduced into the analysis section 4 without volatilizing. Therefore, it is possible to prevent a decrease in analysis accuracy which decrease is caused by volatilization of the mercury.

Figure 3:
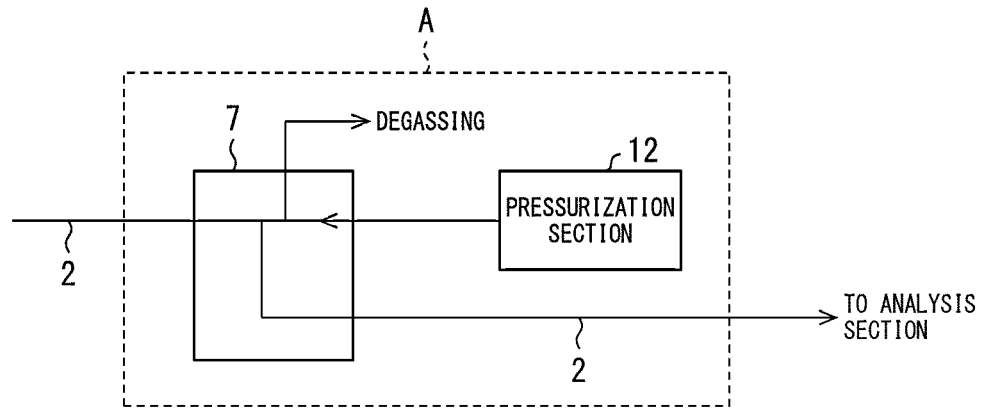
FIG. 3 is a drawing illustrating a part of a configuration of a flow analyzer in accordance with another embodiment of the present invention.
Figure 8:
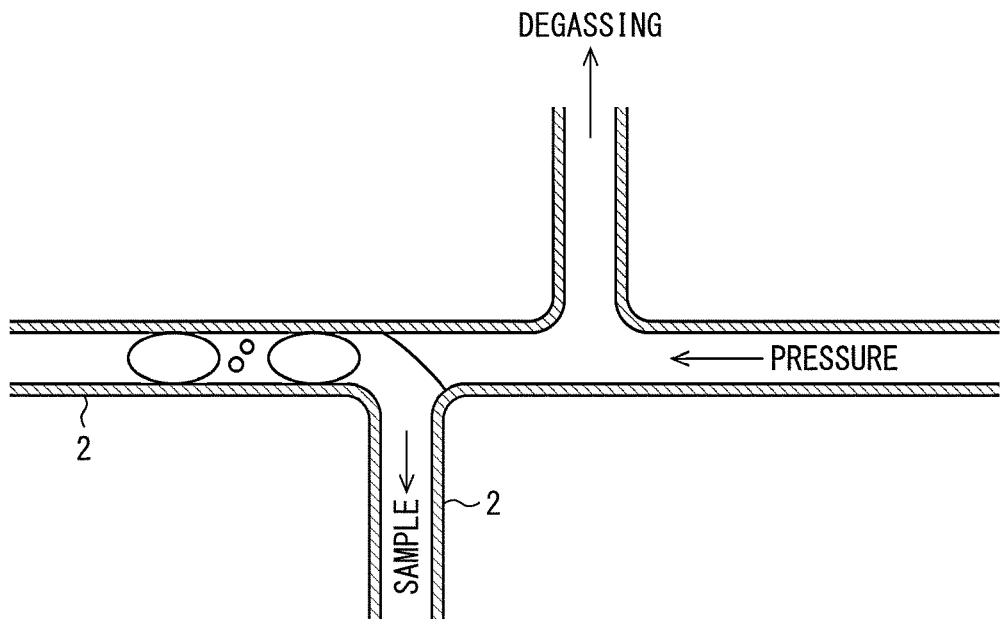
FIG. 8 is a drawing illustrating a part of a configuration of a flow analyzer in accordance with another embodiment of the present invention.

The flow analyzer in accordance with an embodiment of the present invention may include a pressurization section which applies, to the heating section 5 from downstream of the heating section 5, pressure against the flow of the sample. FIGS. 3 and 8 are each a partial schematic drawing illustrating an example of the flow analyzer which includes a pressurization section 12 which applies pressure against the flow of the sample, from downstream of the heating section 5 or downstream of the cooling section 6. In the example illustrated in each of FIGS. 3 and 8, pressure against the flow of the sample is applied from the pressurization section 12 which is provided downstream of the gas-liquid separation section. The pressurization section 12 includes, for example, a compressor and a valve. By providing the pressurization section, it is possible to decompose the sample at high temperature and high pressure in the heating section 5. Therefore, the flow analyzer preferably includes the pressurization section, because it is possible to efficiently decompose an impurity including an organic matter and dissolve mercury in a solution. The pressure applied by the pressurization section 12 is not particularly limited, and may be selected, as appropriate, in accordance with the heating temperature, the heating time, and/or the like in the heating section 5. For example, the pressure is not more than 0.14 MPa, and, in some cases, includes a negative pressure of less than 0.1 MPa. The pressure is more preferably more than 0.1 MPa and not more than 0.13 MPa.

In the flow analyzer in accordance with an embodiment of the present invention, an autosampler can be used as the sample introduction section. Further, an ultrasonic homogenizer or a stirrer may be provided so as to pulverize and/or stir the sample prior to the sampling.

The flow analyzer in accordance with an embodiment of the present invention may further include a dilution section which is provided in the middle of the tube. This makes it possible to automatically carry out desired dilution in the flow analyzer, in a case where it is necessary to dilute the sample depending on the concentration of the sample. As such a dilution section, a commercially available automatic dilution device can be suitably used.

In the flow analyzer in accordance with an embodiment of the present invention, a device which pretreats the sample that is not a liquid but a solid or the like and which thereby prepares a liquid sample may be incorporated in the sample introduction section or provided upstream of the sample introduction section. The flow analyzer is a device which analyzes a liquid sample by a flow analysis method. Thus, it is not possible to measure, as it is, the sample that is not a liquid but a solid or the like. Therefore, by providing the device which pretreats the sample that is not a liquid but a solid and the like and which thereby prepares a liquid sample, it is possible to unintermittedly carry out operations from the pretreatment of the sample that is not a liquid but a solid and the like to the analysis of the sample. As such a device, a device which fully automatically pretreats the sample that is not a liquid but a solid and the like is more preferable. For example, a fully automatic acidolysis pretreating device which fully automatically carries out addition of the reagent, mixing, heating, and dilution in a measuring flask can be suitably used.

<1.2> Embodiment 2

Figure 2:
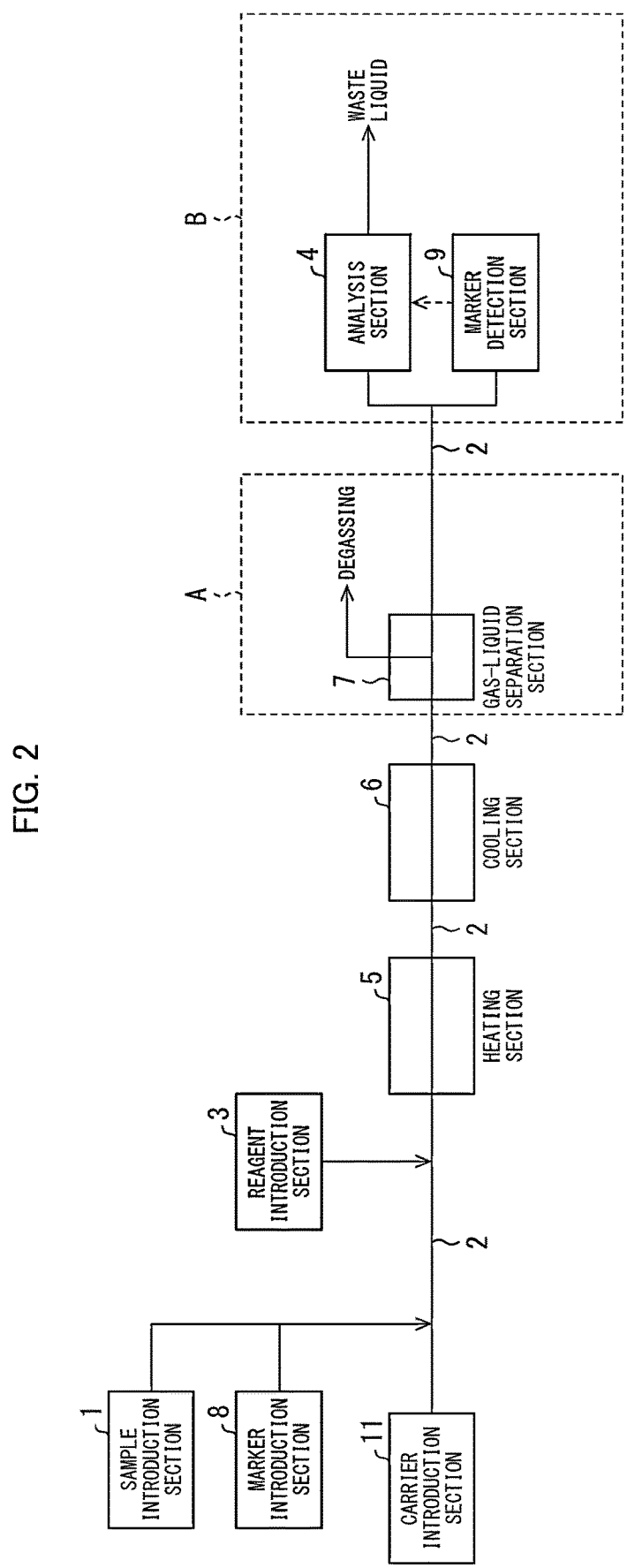
FIG. 2 is a drawing schematically illustrating a configuration of a flow analyzer in accordance with Embodiment 2 of the present invention.

FIG. 2 is a drawing schematically illustrating a configuration of a flow analyzer in accordance with Embodiment 2 of the present invention. Note that, for convenience, members which have the same functions as those of the members that have been described in Embodiment 1 will be given the same reference signs and will not be described again.

The flow analyzer in accordance with Embodiment 2 of the present invention employs a flow injection analysis method (FIA) in which a reagent is introduced into a flow of a sample that is inside a tube and that is not segmented by gas bubbles, a reaction operation is carried out, and then an analysis is carried out by a detector that is provided downstream.

A flow analyzer in accordance with Embodiment 1 of the present invention includes: a carrier introduction section 11 that introduces a carrier into a tube 2; a sample introduction section 1 that is for introducing a sample into a flow of the carrier inside the tube 2; a marker introduction section 8 that is for introducing a marker into the flow of the carrier inside the tube 2; a reagent introduction section 3 that adds a reagent to a flow of the sample which is transferred inside the tube 2; a heating section 5 that carries out a heat treatment with respect to the sample which is transferred inside the tube 2 and to which the reagent has been added; a cooling section 4 that cools the sample which has been subjected to the heat treatment; a gas-liquid separation section 7 that removes gas which is present in the tube after cooling; an analysis section 4 that quantitatively or qualitatively analyzes the sample from which the gas has been removed by the gas-liquid separation section 7; and a marker detection section 9 that detects the marker and outputs a detection signal to the analysis section 4. The analysis section 4 acquires analysis data on the basis of the detection signal.

The flow analyzer in accordance with Embodiment 2 has the same configuration as that of the flow analyzer illustrated in FIG. 1, except that, in the former, the carrier introduction section 11 is provided upstream of the sample introduction section 1 which is for introducing the sample to the tube 2 and the marker introduction section 8 which is for introducing the marker into the tube 2, and a gas bubble segmentation section is not provided.

The flow analyzer in accordance with Embodiment 2 employs the flow injection analysis method (FIA). As such, the carrier introduction section 11 introduces the carrier into the tube 2, and the sample introduction section 1 and the marker introduction section 8 introduce the sample and the marker, respectively, into the flow of the carrier inside the tube 2.

The carrier is not particularly limited, provided that the carrier is a liquid which does not adversely affect a pretreatment and the analysis of the sample. Examples thereof include water, surfactants, acid solutions, and alkaline solutions.

The other configurations of the flow analyzer in accordance with Embodiment 2 are as described in Embodiment 1, and therefore description thereof will be omitted.

<2> Flow Analysis Method

The following description will discuss a flow analysis method in accordance with an embodiment of the present invention. Note that, for convenience, matters which have been already described in <1> Flow analyzer will not be described again.

The flow analysis method in accordance with an embodiment of the present invention includes; a sample introduction step of introducing a sample into a tube; a reagent addition step of adding a reagent to the sample which is transferred inside the tube; and an analysis step of quantitatively or qualitatively analyzing the sample to which the reagent has been added, and further includes: a heating step of carrying out a heat treatment with respect to the sample to which the reagent has been added; a cooling step of cooling the sample which has been subjected to the heat treatment and which is transferred inside the tube; and a gas-liquid separation step of removing gas which is present in the tube after cooling.

The sample introduction step is a step of introducing the sample into the tube. For example, a sampling device samples a plurality of samples and sequentially and continuously introduces them into the tube at a given flow rate.

The reagent addition step is a step of adding the reagent to the flow of the sample that is transferred inside the tube. The reagent is added by the reagent introduction section described above.

The analyzing step is a step of analyzing the sample that is transferred through the tube. Note, here, that the analysis includes detection of the presence or absence of an analysis target or measurement of the concentration of the analysis target. The analysis is not limited to a quantitative analysis or a qualitative analysis. Further, an analysis method is also not particularly limited, and any analysis can be employed. Examples thereof include inductively coupled plasma mass spectrometry, inductively coupled plasma optical emission spectrometry, atomic absorption photometry, inductively coupled plasma triple quadrupole mass spectrometry, an ion electrode analysis method, and spectrophotometry.

The analysis target is also not particularly limited. For example, the analysis target can be various aqueous samples such as tap water, groundwater, seawater, lake water, waste water from factories and the like, ion-exchange water, ultrapure water, reagents, pharmaceuticals, and reagents for use in semiconductors and industries. The flow analysis method in accordance with an embodiment of the present invention brings about an effect that, in a case where an analysis is carried out with mercury as an analysis target, it is possible to, without carrying out a complicated pretreatment, analyze the mercury and analyze a sample containing the mercury with accuracy equivalent to that of the conventional method. The flow analysis method in accordance with an embodiment of the present invention can be suitably used for a simultaneous analysis of metal elements including mercury. Therefore, it is possible to simultaneously analyze mercury, which has been difficult to analyze due to volatilization thereof, and the other metal elements.

The heating step is a step of carrying out a heat treatment with respect to the sample to which the reagent has been added in the reagent addition step. The cooling step is a step of cooling the sample which has been subjected to the heat treatment in the heating step and which is transferred inside the tube. The gas-liquid separation step is a step of removing gas which is present in the tube after cooling in the cooling step. The sample from which the gas has been removed in the gas-liquid separation step is analyzed in the analysis step.

The flow analysis method in accordance with an embodiment of the present invention includes the sample introduction step, the reagent addition step, the heating step, the cooling step, the gas-liquid separation step, and the analysis step, and further includes, between the sample introduction step and the next sample introduction step, a marker introduction step of introducing a marker into the tube. Note, here, that the marker introduction step and the sample introduction step are preferably carried out such that the marker and a given number of samples which given number is one or more are alternately introduced into the tube.

Further, the flow analysis method in accordance with an embodiment of the present invention includes a marker detection step of detecting the marker and outputting a detection signal to the analysis device, and in the analysis step, analysis data is acquired on the basis of the detection signal.

The flow analysis method in accordance with an embodiment of the present invention may be a method in which a continuous flow analysis method (CFA) is used or may be alternatively a method in which a flow injection analysis method (FIA) is used. In a case where the flow analysis method in accordance with an embodiment of the present invention is a method in which the continuous flow analysis method (CFA) is used, the flow analysis method includes a gas bubble segmentation step of producing, in the tube, a plurality of segments that are separated by gas bubbles, by carrying out gas bubble segmentation with respect to the sample and the marker that are introduced into the tube. In a case where the flow analysis method in accordance with an embodiment of the present invention is a method in which the flow injection analysis method (FIA) is used, the flow analysis method can further include a carrier introduction step prior to the sample introduction step and the marker introduction step.

<3> Summary

Embodiments of the present invention include the following.
<1> A flow analyzer including: a sample introduction section that is for introducing a sample into a tube; a reagent introduction section that adds a reagent to the sample which is transferred inside the tube; and an analysis section that quantitatively or qualitatively analyzes the sample to which the reagent has been added, the flow analyzer further including: a heating section that carries out a heat treatment with respect to the sample to which the reagent has been added; a cooling section that cools the sample which has been subjected to the heat treatment and which is transferred inside the tube; and a gas-liquid separation section that removes gas which is present in the tube after cooling.
<2> The flow analyzer as described in <1>, wherein the cooling section includes a tube having a length of 0.5 m to 3 m, and the sample is transferred inside the tube of the cooling section.
<3> The flow analyzer as described in <2>, wherein the tube of the cooling section includes a coil part.
<4> The flow analyzer as described in any one of claims <1> through <3>, further including: a marker introduction section that is for introducing a marker into the tube; and a marker detection section that detects the marker and outputs a detection signal to the analysis section, the analysis section acquiring analysis data on the basis of the detection signal.
<5> The flow analyzer as described in <4>, wherein the marker introduction section and the sample introduction section are configured such that the marker and a given number of samples which given number is one or more are capable of being alternately introduced into the tube.
<6> The flow analyzer as described in any one of <1> through <5>, wherein the analysis section is an inductively coupled plasma mass spectrometer or an inductively coupled plasma optical emission spectrometer.
<7> The flow analyzer as described in any one of <1> through <6>, wherein the reagent includes nitric acid.
<8> The flow analyzer as described in any one of <1> through <7>, wherein the reagent includes hydrochloric acid.
<9> The flow analyzer as described in any one of <1> through <8>, the flow analyzer being a device for measuring a concentration of a metal element including mercury.
<10> The flow analyzer as described in any one of <1> through <9>, further including a gas bubble segmentation section that produces, inside the tube, a plurality of segments separated by gas bubbles, by carrying out gas bubble segmentation with respect to the sample which is introduced into the tube.
<11> A flow analysis method including: a sample introduction step of introducing a sample into a tube; a reagent addition step of adding a reagent to the sample which is transferred inside the tube; and an analysis step of quantitatively or qualitatively analyzing the sample to which the reagent has been added, the flow analysis method further including: a heating step of carrying out a heat treatment with respect to the sample to which the reagent has been added; a cooling step of cooling the sample which has been subjected to the heat treatment and which is transferred inside the tube; and a gas-liquid separation step of removing gas which is present in the tube after cooling.
<12> The flow analysis method as described in <11>, wherein gas bubble segmentation is not carried out after the gas-liquid separation step.

EXAMPLES

The present invention will be described in more detail with reference to examples below. Note, however, that the present invention is not limited to the examples, and the present invention also encompasses, in its scope, any example derived by combining, as appropriate, technical means disclosed in differing examples.

[Device]

Figure 4:
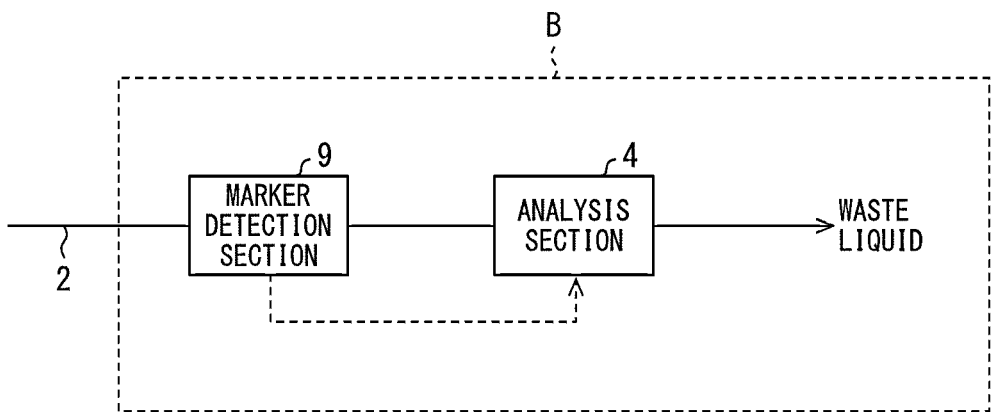
FIG. 4 is a drawing illustrating a configuration of a marker detection section in a flow analyzer in accordance with another embodiment of the present invention.

As a flow analyzer, used was an analyzer that was the flow analyzer illustrated in FIG. 1, the part B, illustrated in FIG. 1, of which had a configuration illustrated in FIG. 4. The flow analyzer includes: a sample introduction section 1 that is for introducing a sample into a tube 2; a marker introduction section 8 that is for introducing a marker into the tube 2; a gas bubble segmentation section 10 that carries out gas bubble segmentation with respect to the sample and the marker which have been introduced into the tube 2; a reagent introduction section 3 that adds a reagent to a flow of the sample which is transferred inside the tube 2; a heating section 5 that carries out a heat treatment with respect to the sample which is transferred through the tube 2; a cooling section 6 that cools the sample which has been subjected to the heat treatment; a gas-liquid separation section 7 that removes gas which is present in the tube after cooling; an analysis section 4 that quantitatively or qualitatively analyzes the sample from which the gas has been removed by the gas-liquid separation section 7; and a marker detection section 9 that detects the marker and outputs a detection signal to the analysis section 4. The analysis section 4 acquires analysis data on the basis of the detection signal. Between the gas-liquid separation section 7 and the analysis section 4, a gas bubble segmentation section that newly introduces gas into the tube is not provided.

Air was used as gas for the gas bubble segmentation, and introduced into the tube 2 every 4 seconds. As the reagent, a mixed solution containing 1 mol/L nitric acid and 1 mol/L hydrochloric acid at a volume ratio of 1:1 was used. As the marker, palladium was used. The palladium was introduced into the tube 2 as a nitric acid acidic solution of palladium (the concentration of palladium: 100 mg/L). The nitric acid acidic solution of the palladium and the sample were alternately introduced into the tube 2. As a detection device of the marker detection section 9, a spectrophotometer (SCIC4000, manufactured by BL TEC K. K.) was used. As an analyzer of the analysis section 4, an inductively coupled plasma mass spectrometer (Agilent 7800 ICP-MS, manufactured by Agilent Technologies Japan, Ltd.) was used.

A pressure of 0.13 MPa, which applied pressure against the flow of the sample, was applied to the heating section 5 from downstream of the heating section 5 by a compressor. A heating temperature in the heating section 5 was set such that the sample had a temperature of 100° C.

A PFA tube having a length of 1.5 m and an inner diameter of 2.0 mm was used for the cooling section 6. The tube was constituted by a linear part having a length of 1.2 m, a coil part having a length of 0.6 m, and a linear part having a length of 0.3 m, in order from the outlet of the heating section 5. The number of turns of the coil part was 5 turns. The coil diameter of the coil part was 40 mm. The coil pitch of the coil part was 3.0 mm. Cooling was carried out by air cooling. The ambient temperature in the cooling section 6 was 15° C.

The marker detection section 9 and the analysis section 4 are disposed in series as illustrated in FIG. 4. The sample which has been subjected to the removal by the gas-liquid separation section 7 is continuously measured by the marker detection section 9 at a stage prior to introduction into the analysis section 4, and then transferred to the analysis section 4. The marker detection section 9 outputted the detection signal to the analysis section 4 upon detection of the marker, and the analysis section 4 started acquiring the analysis data upon receipt of the detection signal.

Example 1: Creation of Calibration Curve

A standard solution containing mercury at a concentration falling within the range of 0.01 µg/L to 1 µg/L was prepared with use of a diluent which was obtained by mixing (i) a mixed solution containing 1 mol/L nitric acid and 1 mol/L hydrochloric acid at a volume ratio of 1:1 and (ii) ultrapure water at a volume ratio of 1:100. A calibration curve was created with the use of the above flow analyzer.

Figure 9:
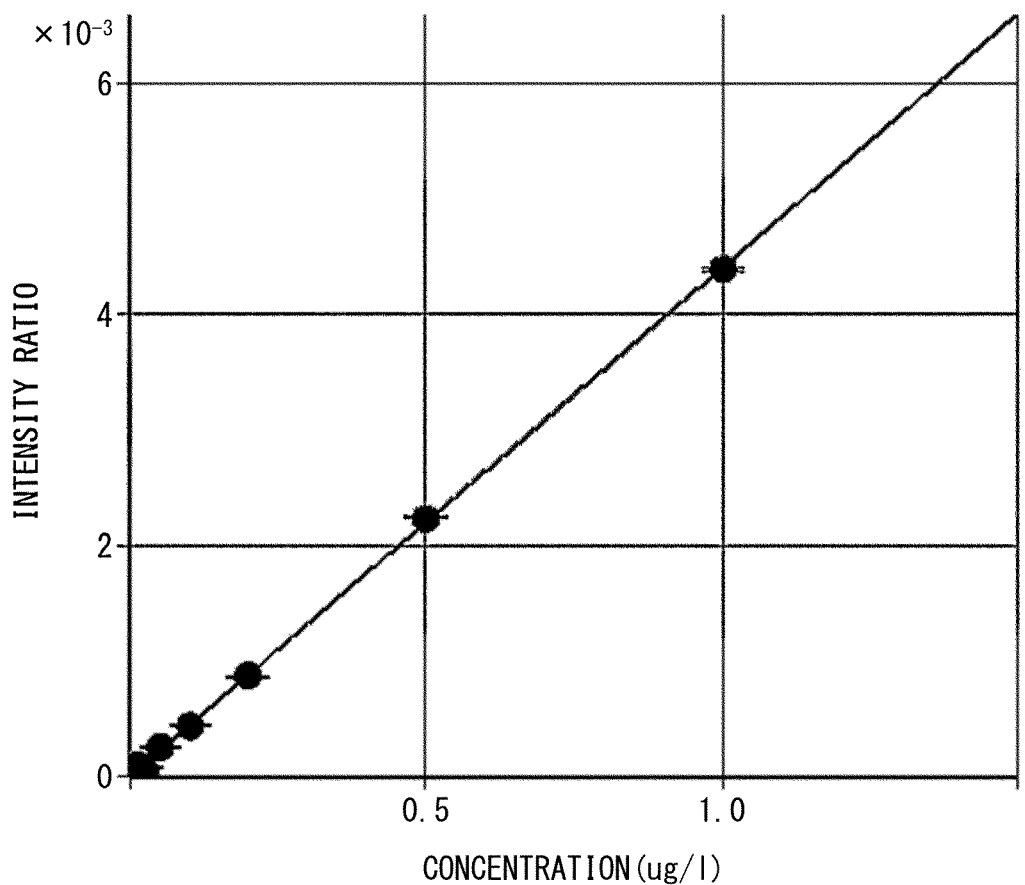
FIG. 9 is a graph showing a calibration curve created in an example.

It was confirmed that the acquired calibration curve showed a good linear relationship, as illustrated in FIG. 9.

Example 2: Analysis of Dam Lake Bottom Water

The concentration of metal elements in a sample were measured with use of the above flow analyzer. As the sample, dam lake bottom water was measured. Further, mercury was added to the sample so that the mercury became 0.05 µg/L and 0.5 µg/L, and addition and recovery tests were carried out.

Table 1 shows measurement results of the sample and results of the addition and recovery tests.

TABLE 1

|  |  | Measurement result (µg/L) | 0.05 µg/L addition and recovery test | | 0.5 µg/L addition and recovery test | |
|---|---|---|---|---|---|---|
|  |  |  | Measurement result (µg/L) | Recovery rate (%) | Measurement result (µg/L) | Recovery rate (%) |
| Example 2 | Dam lake bottom water | 0.0037 | 0.0414 | 75.4 | 0.444 | 88.0 |
| Example 3 | Riverbed water | 0.0028 | 0.0485 | 91.4 | 0.493 | 98.1 |
| Example 4 | Tap water | 0.0041 | 0.0595 | 110.7 | 0.526 | 104.3 |

Example 3: Analysis of Riverbed Water

Measurement of a sample and addition and recovery tests were carried out in the same manner as in Example 2, except that riverbed water was measured as the sample.

Example 4: Analysis of Tap Water

Measurement of a sample and addition and recovery tests were carried out in the same manner as in Example 2, except that tap water was measured as the sample.

As is clear from the results shown in Table 1, high recovery rates were achieved for the dam lake bottom water which contained organic matters in a large amount, the riverbed water, and the tap water. Similar recovery rates are obtained also in analyses carried out by the conventional official method. Thus, it was confirmed that the flow analyzer and the flow analysis method made it possible to analyze a sample containing mercury with accuracy equivalent to that of the conventional method.

INDUSTRIAL APPLICABILITY

According to the present invention, it is possible to provide a flow analyzer and a flow analysis method each of which makes it possible to, without carrying out a complicated pretreatment, analyze mercury and continuously analyze a sample containing mercury with accuracy equivalent to that of the conventional method.

According to such a configuration, it is possible to contribute to reduction of pollution of environmental water, tap water, and the like. Thus, it is possible to contribute to achievement of Goals 14 and 15 of the Sustainable Development Goals (SDGs).

REFERENCE SIGNS LIST

1 Sample introduction section
2 Tube
3 Reagent introduction section
4 Analysis section
5 Heating section
6 Cooling section
7 Gas-liquid separation section
8 Marker introduction section
9 Marker detection section
10 Gas bubble segmentation section
11 Carrier introduction section
12 Pressurization section
13 Gas bubbles
14 Gas bubbles

The invention claimed is:

1. A flow analyzer comprising:
a sample introduction section that is for introducing a sample into a tube;
a reagent introduction section that adds a reagent to the sample which is transferred inside the tube; and
an analysis section that quantitatively or qualitatively analyzes the sample to which the reagent has been added,
said flow analyzer further comprising:
a heating section that carries out a heat treatment with respect to the sample to which the reagent has been added;
a cooling section that cools the sample which has been subjected to the heat treatment and which is transferred inside the tube; and
a gas-liquid separation section that removes gas which is present in the tube after cooling,
the heating section being a thermostatic bath which includes a heater, and a heating temperature in the heating section being set such that the sample has a temperature of not lower than 50° C. and not higher than 140° C.,
the cooling section including a tube having a length of 0.5 m to 3 m, and the sample is transferred inside the tube of the cooling section,
said flow analyzer being a device for measuring a concentration of a metal element including mercury.

2. The flow analyzer as set forth in claim 1, wherein the tube of the cooling section includes a coil part.

3. The flow analyzer as set forth in claim 2, wherein the tube of the cooling section includes a linear part in addition to the coil part, and the coil part is disposed downstream of the linear part.

4. The flow analyzer as set forth in claim 1, further comprising:
a marker introduction section that is for introducing a marker into the tube; and
a marker detection section that detects the marker and outputs a detection signal to the analysis section,
the analysis section acquiring analysis data on the basis of the detection signal.

5. The flow analyzer as set forth in claim 4, wherein the marker introduction section and the sample introduction section are configured such that the marker and a given number of samples which given number is one or more are capable of being alternately introduced into the tube.

6. The flow analyzer as set forth in claim 1, wherein the analysis section is an inductively coupled plasma mass spectrometer or an inductively coupled plasma optical emission spectrometer.

7. The flow analyzer as set forth in claim 1, wherein the reagent contains nitric acid.

8. The flow analyzer as set forth in claim 1, wherein the reagent contains hydrochloric acid.

9. The flow analyzer as set forth in claim 1, further comprising a gas bubble segmentation section that produces, inside the tube, a plurality of segments separated by gas bubbles, by carrying out gas bubble segmentation with respect to the sample which is introduced into the tube.

10. A flow analysis method comprising:
a sample introduction step of introducing a sample into a tube;
a reagent addition step of adding a reagent to the sample which is transferred inside the tube; and
an analysis step of quantitatively or qualitatively analyzing the sample to which the reagent has been added,
said flow analysis method further comprising:
a heating step of carrying out a heat treatment with respect to the sample to which the reagent has been added;
a cooling step of cooling the sample which has been subjected to the heat treatment and which is transferred inside the tube; and
a gas-liquid separation step of removing gas which is present in the tube after cooling,
the heat treatment being carried out in a thermostatic bath which includes a heater, and a heating temperature in the heat treatment being set such that the sample has a temperature of not lower than 50° C. and not higher than 140° C.,
in the cooling step, the sample which has been subjected to the heat treatment and which is transferred inside the tube being cooled while being transferred inside a tube of a cooling section which tube has a length of 0.5 m to 3 m, and
said flow analysis method being a method for measuring a concentration of a metal element including mercury.

11. The flow analysis method as set forth in claim 10, wherein gas bubble segmentation is not carried out after the gas-liquid separation step.

* * * * *